United States Patent [19]

Swartout

[11] 4,274,885
[45] Jun. 23, 1981

[54] METHOD FOR WASHING CENTRIFUGAL ANALYZER TEST DISKS

[76] Inventor: Bobbye J. Swartout, Rte. 2 Box 326, Etowah, Tenn. 37331

[21] Appl. No.: 59,119

[22] Filed: Jul. 19, 1979

[51] Int. Cl.³ ............................................. B08B 5/04
[52] U.S. Cl. ........................................ 134/21; 15/304; 134/22 R; 134/24; 422/72
[58] Field of Search .................... 134/24, 21, 22 R; 422/72; 15/302, 304, 395

[56] References Cited

U.S. PATENT DOCUMENTS

| | | | |
|---|---|---|---|
| 963,767 | 7/1910 | Jarvis | 134/21 |
| 3,173,434 | 3/1965 | Bender | 134/21 |
| 3,679,367 | 7/1972 | Negersmith et al. | 422/72 |
| 3,836,329 | 9/1974 | Jordan | 134/21 |
| 3,879,795 | 8/1975 | Gfeller | 134/21 |
| 3,880,592 | 4/1975 | Kelley et al. | 422/72 |
| 3,901,658 | 8/1975 | Burtis et al. | 422/72 |

Primary Examiner—S. Leon Bashore
Assistant Examiner—Michael L. Goldman
Attorney, Agent, or Firm—Alan Ruderman

[57] ABSTRACT

A washing device for a centrifugal analyzer testing disk having a multiplicity of test cells each of which has a specimen and a reactant receiving hole communicating with the cell. The washing device has a washer body member with a multiplicity of fingers each receivable within the speciman receiving hole of each cell. Each finger has a bore communicating with a plenum within the body member. The body member communicates with tubing to a low pressure source such as a T-connector which can be connected to a faucet at one end to create a suction within the body member and draw cleaning solution through the reactant receiving hole of the test cell and out the specimen receiving hole when the disk is immersed in a cleaning solution.

2 Claims, 4 Drawing Figures

METHOD FOR WASHING CENTRIFUGAL ANALYZER TEST DISKS

BACKGROUND OF THE INVENTION

This invention relates to cleaning apparatus and more particularly to apparatus for washing cellular testing members of multi-test chemical centrifugal analyzers.

Centrifugal analyzers for separating and chemically testing liquid suspended particulate materials such as blood use a disk shaped testing member having a multiplicity of individual cells. The cells emanate radially from a hub adjacent a central opening which is positionable on a driven rotatable member of the analyzer to provide the required centrifugal separating force. Each cell includes a pair of spaced holes on a face of the disk communicating with the hollow interior thereof so that blood or other specimen to be tested may be desposited into one hole and a fluid chemical reactant deposited into the other hole of each cell.

Current hospital practice is to use each disk once and to discard it because a quick and thorough method of washing the residue from each cell has been unavailable. When one considers that a large modern hospital may use upwards of one thousand such cellular disks each month it is readily seen that substantial savings may be realized by effectively cleaning and reusing the disks.

SUMMARY OF THE INVENTION

Consequently, it is a primary object of the present invention to provide an apparatus and method for washing quickly and effectively the cellular testing disks of centrifugal analyzers.

It is another object of this invention to provide an apparatus and method for washing each of the cells of a multi-cell centrifugal analyzer test disk.

It is a further object of this invention to provide an apparatus and method for drawing a washing solution through the specimen and reactant deposit holes of each test cell of a multi-cell centrifugal analyzer test disk to clean the cells for reuse.

In achieving these objects the present invention provides a cleaning apparatus comprising a washer body member having a multi-plicity of male projections or fingers each adapted to be snugly received within one of the specimen or reactant holes of each cell, each finger having a passage-way communicating with a plenum or manifold within the body member and means communicating the plenum with sub-atmospheric pressure. The disk is immersed in the cleaning solution which enters one hole and is drawn through the other hole of each cell. Although the fingers may cooperate with either the specimen or reactant receiving hole to draw the washing solution out of the cells it has been found that the better results are obtained when the solution enters the holes which are disposed radially further from the center of the disk and drawn out the holes disposed closer to the disk center. In the preferred form the body member manifold simply communicates with tubing to which a slight suction is applied. As the solution flows through each cell the cells are cleansed for reuse.

Therefore, yet another object of this invention is to provide apparatus and method for washing a multi-cell centrifugal analyzer test disk, said apparatus having a hollow body member with a multiplicity of fingers each snugly receiveable within an aperture on the face of the disk, each finger having a passageway communicating with the hollow, and means for communicating the hollow with a low pressure source, said method comprising immersing the disk into a bath of cleaning solution and drawing the solution through each cell, through the fingers into the hollow and then out of the hollow.

BRIEF DESCRIPTION OF THE DRAWINGS

The particular features and advantages of the invention as well as other objects will become apparent from the following description taken in connection with the accompanying drawings, in which.

DESCRIPTION OF THE PREFERRED EMBODIMENT

Figure 1:
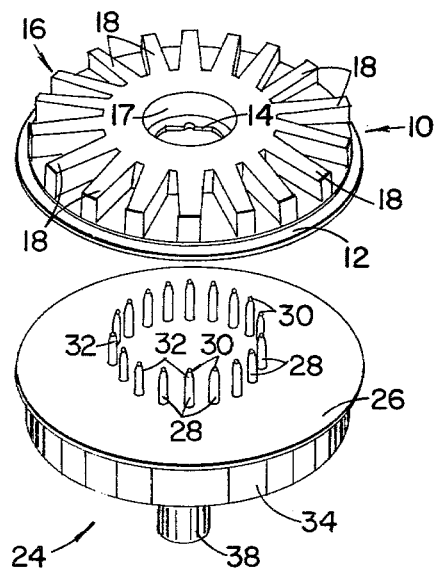
FIG. 1 is a perspective view of the cellular testing disk and a washer body member constructed in accordance with the principles of the present invention.
Figure 2:
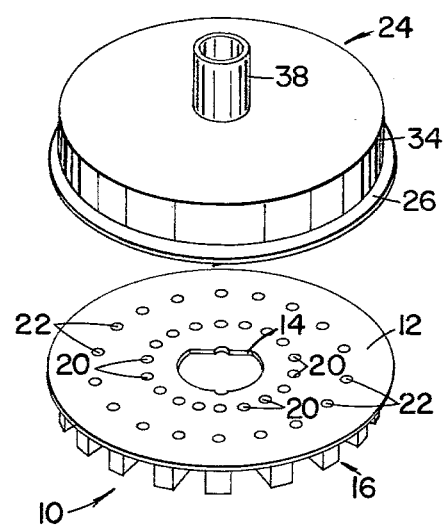
FIG. 2 is a view similar to FIG. 1, but with the parts inverted.
Figure 3:
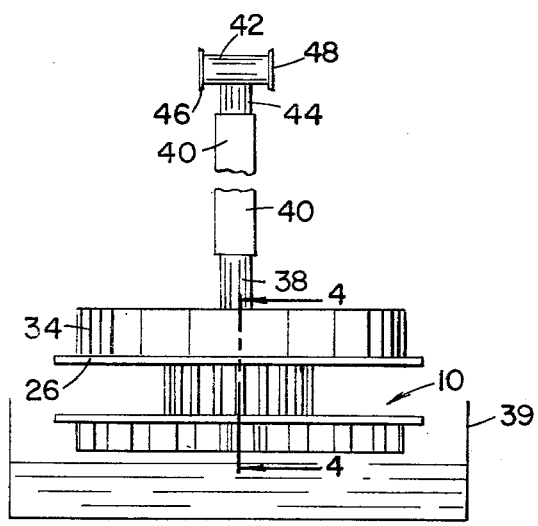
FIG. 3 is an elevational view of the preferred form of the disk washing apparatus.
Figure 4:
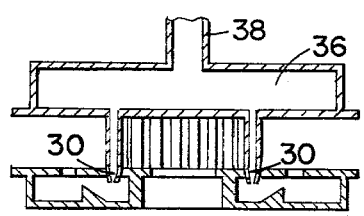
FIG. 4 is a cross sectional view taken through the washer body member substantially along line 4—4 of FIG. 3.

Referring now to the drawings, a testing disk 10 utilized with centrifugal analyzers comprises a planar disk portion 12 having a central aperture 14 of a shape adapted to be received on a driven rotatable hub (not shown) of the analyzer. The testing disk also includes an enclosure member 16 having a central bore 17 and a multiplicity of radially extending channel-like spurs 18 bonded to the disk portion 12. Each of the spurs 18 is hollow and together with the cooperating portion of the disk portion 12 forms an individual test cell so that a multi-plicity of tests can be performed simultaneously. A first hole 20 radially spaced from the aperture 14 is formed in the disk portion 12 and opens into each of the cells for receiving the test specimen. A second series of holes 22 is similarly formed in the disk portion radially from the holes 20 for receiving the chemical reactant.

The washer body member 24 comprises a plastic or rubber-like materal having a substantially planar portion 26 of any convenient shape, preferably circular and similar in size to that of the planar disk portion 12 of the testing disk 10. The planar portion 26 includes a multiplicity of fingers members 28, there being one for each test cell of the testing disk 10. Each of the fingers 28 has a central bore 30 and is of a size to fit snugly within one of the holes 20 or 22 of each cell and may include a tapered tip 32 for this purpose. Preferably the fingers are receivable within the holes 20 and are thus radially spaced from the center of the disk 26 accordingly. The body member 24 also includes a substantially cup-shaped portion 34 which is bonded or otherwise secured to the planar portion 26 to provide a hollow manifold or plenum 36 in the body member. A substantially centrally located small annular hub 38 is formed on the surface of the cup-shaped portion 34 remote from the portion 26 and communicates with the plenum 36.

To wash the test disk 10, the washer body member is positioned so the fingers are within the holes 20 and the test disk is inserted into a tub of water or other cleaning solution 39. The solution is then drawn into the holes 22 and out the holes 20 through the fingers by applying a lower pressure to the plenum then the pressure of the solution. To provide the suction, a tube 40 is fitted at one end about the hub 38 and about its other end to any suitable low pressure source. For simplicity, it is preferred to connect the tube 40 to a T-connector 42 at the central leg 44. The inlet end 46 of the T-connector may then be attached to the faucet of a sink and when pressurized water flows through the connector and out the outlet end 48, a low pressure is created in the leg 44 which draws the cleaning solution through the cells, into the hollow 36 and up the tube 40 where it enters the leg 44 of the T-connector. The fluid thus enters the connector and flows out the outlet 48 with the water from the faucet.

Numerous alterations of the structure herein disclosed will suggest themselves to those skilled in the art. However, it is to be understood that the present disclosure relates to the preferred embodiment of the invention which is for purposes of illustration only and not to be construed as a limitation of the invention. All such modifications which do not depart from the spirit of the invention are intended to be included within the scope of the appended claims.

Having thus set forth the nature of the invention what is claimed herein is:

1. The method of washing a centrifugal analyzer test disk having a multiplicity of radially extending test cells, each cell having a first and a second radially spaced aperature communicating with the cell interior, said method comprising:

inserting into one of the first and second apertures of each cell a finger having a through bore so the bore is in flow communication with the respective cell, immersing said disk in a bath of washing solution so the solution may enter the other of said first and second apertures, and applying to the fingers a pressure lower than that of the bath to draw said solution through the cells with the fingers.

2. In the method as recited in claim 1, wherein the fingers communicate with a hollow body member, said lower pressure being applied to said body member to draw said solution into said body member, and removing said solution from said body member.

* * * * *